US00PP25995P3

(12) United States Plant Patent
Hancock

(10) Patent No.: US PP25,995 P3
(45) Date of Patent: Oct. 20, 2015

(54) BLUEBERRY PLANT DENOMINATED 'CALYPSO'

(50) Latin Name: *Vaccinium corymbosum*
Varietal Denomination: Calypso

(71) Applicant: Board of Trustees of Michigan State University, East Lansing, MI (US)

(72) Inventor: James F. Hancock, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 82 days.

(21) Appl. No.: 13/998,453

(22) Filed: Nov. 1, 2013

(65) Prior Publication Data

US 2015/0128312 P1 May 7, 2015

(51) Int. Cl.
*A01H 5/08* (2006.01)

(52) U.S. Cl.
USPC ..... Plt./157

(58) Field of Classification Search
USPC ..... Plt./157
CPC ..... A01H 5/08
See application file for complete search history.

*Primary Examiner* — Kent L Bell
(74) *Attorney, Agent, or Firm* — Cochran Freund & Young, LLC

(57) ABSTRACT

'Calypso' is a new blueberry cultivar of primarily *Vaccinium corymbosum*. The rest of its parentage is from *V. darrowii* (13.3%), *V. angustifolium* (3.8%), *V. tenellum* (<1%), and *V. ashei* (<1%). It is a highly productive cultivar with excellent fresh fruit quality. Plants of 'Calypso' are vigorous and upright. Its canes are numerous and moderately branched, and the fruit are well exposed. Its berries are large, have small, dry picking scars, medium light blue color, and excellent firmness and flavor. In general, the fruit of 'Calypso' has held extremely well on the bush after ripening, except in the unusually hot summers of 2012 in Michigan and Oregon. In that year it was softer than normal, performing similar to 'Liberty' under hot conditions.

5 Drawing Sheets

Latin name and variety denomination: The present disclosure relates to a new and distinct variety of *Vaccinium corymbosum*, which is hereby denominated 'Calypso.'

SUMMARY

The present disclosure relates to a new and distinct variety of highbush blueberry plant, denominated 'Calypso.' 'Calypso' is primarily *Vaccinium corymbosum* with 13.3% of its genes coming from *V. darrowii,* 3.8% from *V. angustifolium*, and <1% from *V. tenellum* and *V. ashei*. It is a highly productive cultivar with excellent fresh fruit quality. Plants of 'Calypso' are vigorous and upright. Its canes are numerous and moderately branched, and the fruit are well exposed. Its berries are large, have small, dry picking scars, medium light blue color, and excellent firmness and flavor. In general, the fruit of 'Calypso' holds extremely well on the bush after ripening, except in the unusually hot summers, as occurred in 2012 in Michigan and Oregon. In that year it was softer than normal; performing similar to 'Liberty' under hot conditions.

BRIEF DESCRIPTION OF THE DRAWINGS

The present variety will become more fully understood from the detailed description and the accompanying drawings, wherein.

DETAILED BOTANICAL DESCRIPTION

The following is a detailed botanical description of the new and distinct variety of blueberry denominated 'Calypso,' its flowers, fruit, and foliage.

Figure 1:
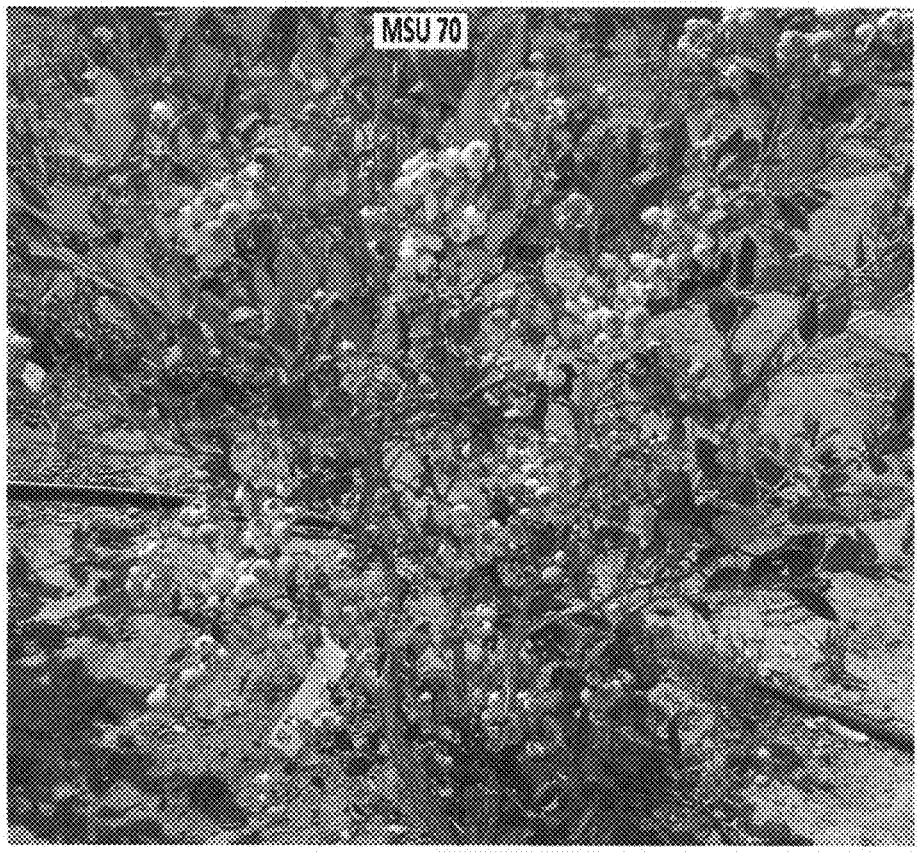
FIG. 1 is a photographic print in full color of a first 'Calypso' blueberry bush, wherein the grasses on the ground are not part of the 'Calypso' blueberry bush.
Figure 2:
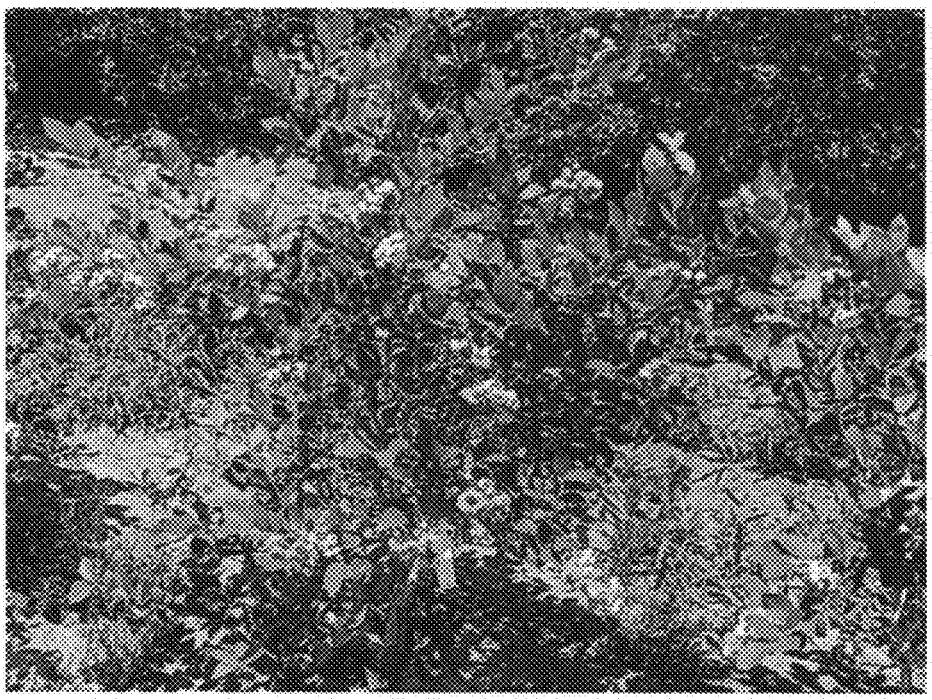
FIG. 2 is a photographic print in full color of a second 'Calypso' blueberry bush, wherein the grasses on the ground, the bushes in the background and the branches projecting from the right edge are not part of the 'Calypso' blueberry bush.
Figure 3:
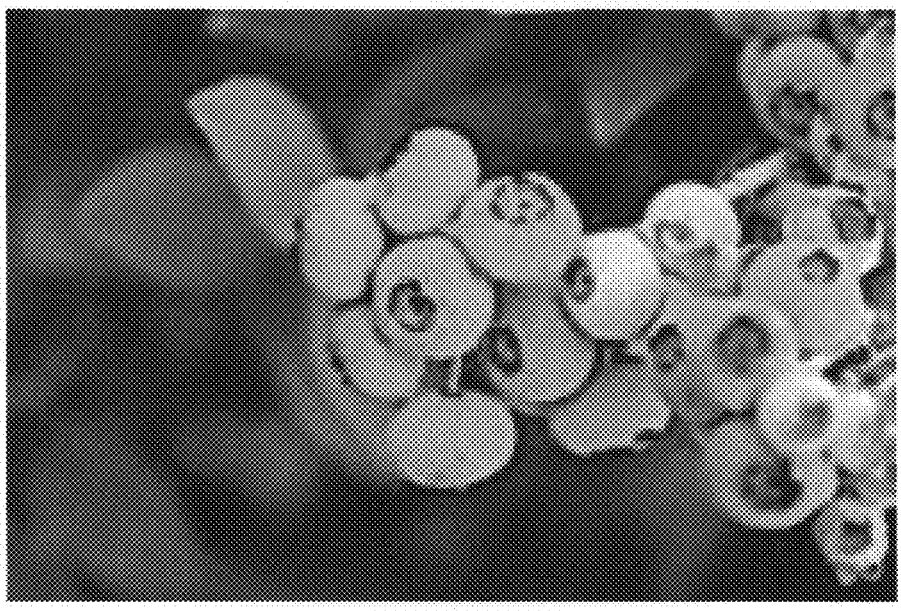
FIG. 3 is a photographic print in full color illustrating a first 'Calypso' branch with exemplary fruit clusters, wherein most, but not all, of the fruit shown is mature.
Figure 4:
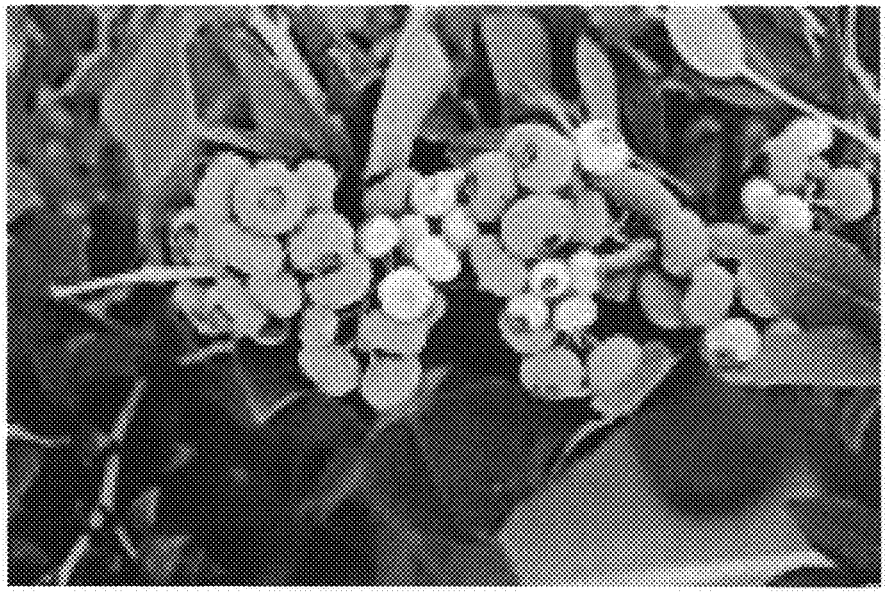
FIG. 4 is a photographic print in full color illustrating a second 'Calypso' branch with exemplary fruit clusters, wherein most, but not all, of the fruit shown is mature.
Figure 5:
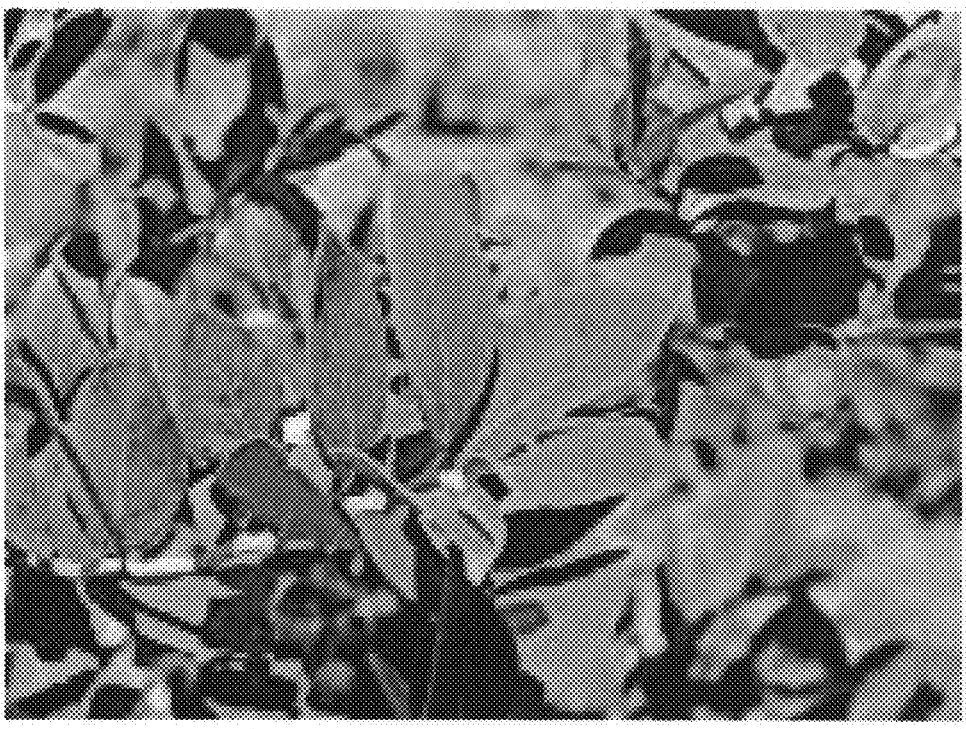
FIG. 5 is a photographic print in full color illustrating a 'Calypso' branch with exemplary leaves, wherein the plants on the ground in the background are not part of the 'Calypso' blueberry bush.

'Calypso' is primarily *Vaccinium corymbosum* with 13.3% of its genes coming from *V darrowii,* 3.8% from *V angustifolium*, and <1% from *V tenet/um* and *V ashei*. Emasculated flowers of 'Draper,' the female parent (i.e., the seed parent), were pollinated in 2002 with pollen from 'Elliott'. The seeds were germinated, grown in a greenhouse for 1 year, and then field planted at Benton Harbor, Mich. 'Calypso' was first selected from a group of 83 siblings in 2006. The selected 'Calypso' plant was first asexually reproduced by cuttings taken from Benton Harbor, Mich. and rooted in East Lansing, Mich. FIG. 1 and FIG. 2 show exemplary 'Calypso' bushes, FIG. 3 and FIG. 4 show 'Calypso' branches with exemplary fruit clusters, and FIG. 5 shows exemplary leaves from a 'Calypso' bush.

The original selection of 'Calypso' was evaluated at Benton Harbor, Mich. for four years. Softwood cuttings were also set in advanced trials at Grand Junction, Mich., South Haven, Mich., Silverton, Oreg., Corvallis, Oreg., Lowell, Oreg., and Osorno, Chile. Two year old plants were set at 4×10 foot spacing in 2008 in Michigan, and in 2009 in Oregon and Chile. As discussed below, the plantings in Michigan were evaluated for three years, and those in Oregon and Chile for two years.

'Calypso' is moderately self-fertile but requires pollination from another highbush blueberry cultivar for maximum fruit development.

'Calypso' may be propagated by hardwood cuttings in a greenhouse and then planted in the field. Initiation of root development from hardwood cuttings may take about four to six weeks.

Initiation of root development from microshoots takes about three to four weeks. Such methods are discussed in the following references, incorporated by reference herein: Doran, W. L. and Bailey, J. S. "Propagation of the high bush blueberry by softwood cuttings," Bulletin Massachusetts Agricultural Experiment Station; no. 410. Amherst, Mass. Massachusetts State College, 1943; Doehlert, C. A "Propagating blueberries from hardwood cuttings," Circular (New Jersey Agricultural Experiment Station) 490. New Brunswick, N.J. New Jersey Agricultural Experiment Station, 1945; Doehlert, C. A. "Propagating blueberries from hardwood cuttings," Circular (New Jersey Agricultural Experiment Station) 551. New Brunswick, N.J.: New Jersey Agricultural Experiment Station, 1953; Zimmerman, R. H. 1991. Micropropagation of temperate zone fruit and nut crops. In: Debergh, P. C. and Zimmerman, R. H. (eds.) Micropropagation: Technology and application. Kluwer, Dordreckt; El Shiekh, A.; Wildung, D. K.; Luby, J. J.; Sargent, K. L.; Read, P. E. "Long term effects of propagation by tissue culture or softwood single node cuttings on growth habit, yield, and berry weight of 'Northblue' blueberry," Journal of the American Society for Horticultural Science. 1996, 121: 2, 339 342; Galletta, G. J.; Ballington, J. R.; Daubeny, H. A; Brennan, R. M.; Reisch, B. J.; Pratt, C.; Ferguson, A R.; Seal, A. G.; McNeilage, M. A.; Fraser, L. G.; Harvey, C. F.; Beatson, R. A.; Hancock, J. F.; Scott, D. H.; Lawrence, F. J.; Janick, J. (ed.); Moore, J. N. "Fruit breeding. Volume II. Vine and small fruits," Department of Horticulture, Purdue University, West Lafayette, Ind. 1996 John Wiley and Sons; New York; USA; Strik, B.; Brun, C.; Ahmedullah, M.; Antonelli, A.; Askham, L.; Barney, D.; Bristow, P.; Fisher, G.; Hart, J.; Havens, D. Draper A D. and Chandler C. K. "Accelerating highbush blueberry selection evaluation by early propagation," Journal of the American Society for Horticultural Science. 1986 111 (2): 301-303; Pritts M. P. and Hancock J. F. (Eds.) "Highbush blueberry production guide," Northeast Regional Agricultural Engineering Service, Ithaca, N.Y., USA 1992.

The fruiting season of 'Calypso' is late mid-season, probably overlapping with 'Jersey' and 'Legacy.' Its overall fruit quality is rated much higher than 'Jersey.' Its fruit are larger than 'Legacy' and it has more highly-rated overall fruit quality and a sweeter taste than the fruit of 'Legacy.' It is not as vigorous as 'Legacy,' but it is more winter hardy, so its yields in Michigan have generally been higher than those of 'Legacy.' 'Calypso' is likely well adapted to all northern highbush production areas, except where summer temperatures are routinely above 30° C. 'Calypso' can be a late mid-season alternative to 'Jersey' and 'Legacy.'

'Calypso' is intended for all northern highbush production areas, except where summers are very hot, such as central Chile, near Chillan and further north. It provides a late mid-season alternative to 'Legacy' and 'Jersey' with good winter hardiness. It has a very upright habit, high yields, and excellent fruit quality, i.e., very large, small scar, extremely firm and crisp, and excellent flavor that is balanced sweet. However, 'Calypso' may not be well adapted to the hotter northern production regions and may produce high numbers of small berries in some years.

'Calypso' characteristics are set forth in Table 1, below. Taxonomic characteristics disclosed herein are standard in the practice (R E Gough, R J Hindle, and V G Shutak, "Identification of Ten Highbush Blueberry Cultivars using Morphological Characteristics," *HortScience* 11 (5): 512-4, 1976). Color descriptions, except those given in common terms, are presented in Royal Horticultural Society Colour Chart designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table 1 are applicable only to mature fruit.

TABLE 1

'Calypso' Characteristics

| Characteristic | 'Calypso' |
|---|---|
| Plant traits | |
| Mature height | 1.3 m |
| Mature width | 0.9 m |
| Height/width ratio | 1.43 |
| Growth habit | upright |
| Annual renewal canes | 3 to 5 |
| Internode length on spring shoots | 1-2.25 cm (1.68 cm average) |
| Mature cane color | grayed-green (198A) |
| Mature cane length | 0.80-1.10 m (0.98 m average) |
| Mature cane width | 1.4 -1.6 cm (1.5 cm average) |
| Bark texture | rough |
| Vigor | strong |
| Fall color on new shoots | |
| One-year-old shoot color | green (144D) |
| One-year-old shoot: length of internode | 15-22 mm (18.0 mm average) |
| Fruiting type | on one-year-shoots only |
| Time of vegetative bud burst | early to mid-May |
| Time of beginning of flowering on one-year-old shoot | late April to mid-May |
| Time of beginning of fruit ripening on one-year-old shoot | early to mid-July |
| Foliage | |
| Leaf shape | elliptic |
| Apex shape | acute |
| Base shape | rounded |
| Leaf length | 4.4-5.0 cm (5 cm average); medium |
| Leaf width | 2.1-2.8 cm (2.4 cm average); medium |
| Leaf length/width ratio | 2.1; medium |
| Leaf margin | entire |
| Leaf nectaries | absent |
| Pubescence | none |
| Color upper surface | green (137A) |
| Intensity of green on upper surface | medium |
| Color lower surface | green (138B) |

TABLE 1-continued

| 'Calypso' Characteristics | |
|---|---|
| Characteristic | 'Calypso' |
| Petiole length | 1-2 cm (1.7 cm average) |
| Petiole diameter | 1.5-2.2 mm (1 8 mm average) |
| Petiole color | light yellowish green (142C) |
| Bud | |
| Bud shape | ovate |
| Bud width | 3.0-4.0 mm (3.8 mm average) |
| Bud length | 5.0-6.0 mm (5.2 mm average) |
| Color | grayed-green (197B) |
| Flower bud anthocyanin coloration | absent |
| Inflorescence length (excluding peduncle) | 2.2-3.1 cm (2.5 cm average) |
| Blossoms | |
| Shape of corolla | elongate-urceolate |
| Size of corolla tube: length | 10-11 mm (10.5 mm average) |
| Size of corolla tube: diameter | 6-7 mm (6.4 mm average) |
| Anthocyanin coloration of corolla tube | absent |
| Petals | 5 (fused) |
| Petal length | 10-11 mm (10.5 mm average) |
| Calyx | 5 lobed |
| Style length | 9-10 mm at corolla tip |
| Color of open flower | white |
| Flower # per cluster | 6-7 |
| Pistil | one per flower |
| Pistil color | yellowish green (145A) |
| Pistil length | 9-10 mm |
| Flower diameter | 6-7 mm |
| Flower length | 10-11 mm |
| Fragrance | faint blueberry aroma |
| Calyx diameter | 5 mm |
| Sepals | fused, 5 lobes |
| Color top | yellowish green (146C) |
| Color bottom | yellowish green (146C) |
| Unripe fruit: intensity of green color | medium |
| Reproductive organs | |
| Type | berry |
| Seed size | 1.32 mm |
| Number of seeds | 5-32 (12.7 average) |
| Mature fruit | |
| Size | large |
| Height | 1.0-1.2 cm (1.1 cm average) |
| Width | 1.5-1.7 cm (1.6 cm average) |
| Shape in longitudinal direction | round |
| Diameter of calyx basin | 6-7 mm (6.4 mm average) |
| Depth of calyx basin | 1.0-2.0 mm (1.4 mm average) |
| Color with bloom | violet blue (98D) |
| Color without bloom | violet blue (103A) |
| Color of skin after removal of bloom | violet blue (103A) |
| Intensity of bloom | strong |
| Firmness | very firm |
| Pedicel scar size | 1.5-2.0 mm (1.8 mm average) |
| Pedicel length | 7-8 mm |
| Pedicel color | yellowish green (144B) |
| Peduncle length | 11-13 mm |
| Peduncle color | yellowish green (138A) |
| Average weight | 2.44 g |
| Sepals | none remaining on ripe fruit |
| Cluster density | medium |
| Sweetness | medium |
| Acidity | medium |

In multi-state trials, 'Calypso' is an upright bush that ripens in the late mid-season, as illustrated in Table 2, below. Specifically, development and fruit characteristics of 'Calypso' were evaluated in 2010, 2011, and 2012 at two locations in Michigan, three in Oregon, and one in Chile. Two year old plants were set in 2008 in Michigan, and 2009 in Oregon and Chile. Evaluations were made when the bushes were 30-50% ripe. Its fruit have good color, a good to excellent scar, and excellent firmness and flavor. It has generally produced high yields of very large fruit, although a high number of small berries were reported in Oregon in 2011. This is a characteristic that is also not unusual in the widely planted 'Liberty.'

TABLE 2

Development and Fruit Characteristics
For bush habit: 1 = sprawling, 5 = semi-erect, and 9 = upright.
For season: 1 = very early, 4-5 = midseason, and 9 = very late.
For vigor and fruit characteristics: 1-4 = inferior, 5-6 = acceptable, 7 = good, 8 = excellent, and 9 = superior.

| State | City | Year | Habit | Season | Yield |
|---|---|---|---|---|---|
| Michigan | Grand Junction | 2010 | 7 | 5 | 8 |
| | | 2011 | 7 | 6 | 6 |
| | | 2012 | 8 | 6 | 8 |
| | South Haven | 2010 | 6 | 5 | 7 |
| | | 2011 | 8 | 6 | 7 |
| | | 2012 | 8 | 5 | 9 |
| | | Mean | 7.3 | 5.5 | 7.5 |
| Oregon | Corvallis | 2010 | 6 | 7 | 8 |
| | | 2011 | 8 | 4 | 8 |
| | Lowell | 2010 | 8 | 5 | 8 |
| | | 2011 | 8 | 5 | 8 |
| | Silverton | 2010 | 9 | 7 | 8 |
| | | 2011 | 8 | 6 | 8 |
| | | Mean | 7.8 | 5.7 | 8.0 |
| Chile | Osorno | 2010 | 7 | 6 | 8 |
| | | 2011 | 6 | 4 | 7 |
| | | Mean | 6.5 | 5.0 | 7.5 |
| | Grand Mean | | 7.2 | 5.4 | 7.7 |

| | | | Fruit characteristics | | | | |
|---|---|---|---|---|---|---|---|
| State | City | Year | Size | Color | Scar | Firm-ness | Flavor |
| Michigan | Grand Junction | 2010 | 8 | 8 | 8 | 8 | 7 |
| | | 2011 | 9 | 6 | 8 | 8 | 7 |
| | | 2012 | 7 | 8 | 8 | 8 | 8 |
| | South Haven | 2010 | 8 | 7 | 8 | 9 | 8 |
| | | 2011 | 8 | 7 | 7 | 9 | 8 |
| | | 2012 | 7 | 7 | 9 | 7 | 8 |
| | | Mean | 7.8 | 7.2 | 8.0 | 8.2 | 7.7 |
| Oregon | Corvallis | 2010 | 7 | 7 | 7 | 6 | 7 |
| | | 2011 | 8 | 8 | 8 | 8 | 8 |
| | Lowell | 2010 | 7 | 7 | 8 | 8 | 8 |
| | | 2011 | 6[1] | 8 | 6 | 8 | 7 |
| | Silverton | 2010 | 7 | 7 | 6 | 6 | 7 |
| | | 2011 | 8 | 7 | 7 | 8 | 7 |
| | | Mean | 7.2 | 7.3 | 7.0 | 7.3 | 7.3 |
| Chile | Osorno | 2010 | 9 | 6 | 7 | 8 | 5 |
| | | 2011 | 8 | 8 | 8 | 9 | 9 |
| | | Mean | 8.5 | 7.0 | 7.5 | 8.5 | 7.0 |
| | Grand Mean | | 7.8 | 7.2 | 7.5 | 8.0 | 7.3 |

In comparative Michigan trials, 'Calypso' bloomed and ripened with 'Legacy,' a little after 'Jersey' and before 'Liberty,' as illustrated in Table 3, below. Specifically, mean fruit rating and ranges of 'Calypso,' 'Legacy,' and 'Liberty' were evaluated at Grand Junction and South Haven, Mich. in 2010, 2011, and 2012. Two year old plants were set in 2008 at 4×10 foot spacing with 8-15 other variety selections. Fruit evaluations were made when the bushes were 50% ripe. It had higher crop loads than 'Jersey' and 'Legacy,' but not 'Liberty.' 'Calypso's' fruit scar and firmness was similar to 'Liberty'. 'Calypso's' fruit were firmer and had smaller fruit scars than 'Jersey' and 'Legacy.' Its flavor was ranked higher than all the others except 'Liberty,' and its color was judged comparable to 'Legacy,' lighter than 'Jersey' and darker than 'Liberty.' 'Calypso's' vigor was not quite as high as the other three cultivars, but it was rated good to very good.

TABLE 3

Mean Fruit Rating and Ranges
The rating scale is 1-9, with 1-4 = inferior, 5-6 = acceptable, 7 = good, 8 = excellent and 9 = superior.
Ranges are in parentheses.

| Cultivar | Date Full bloom | Date 50% ripe | Plant vigor | Weight |
|---|---|---|---|---|
| 'Calypso' | 5/13 (4/28-5/20) | 7/10 (7/3-7/18) | 7.5 (7-8) | 7.8 (7-9) |
| 'Jersey' | 5/7 (4/24-5/12) | 7/4 (6/22-7/11) | 8.0 (all 8s) | 5.6 (5-6) |
| 'Legacy' | 5/11 (4/28-5/15) | 7/9 (6/28-7/15) | 8.5 (8-9) | 8.0 (all 8s) |
| 'Liberty' | 5/15 (4/28-5/23) | 7/26 (7/17-7/30) | 8.0 (7-9) | 7.6 (7-8) |

| Cultivar | Color | Picking scar | Firmness | Flavor | Fruit load[1] |
|---|---|---|---|---|---|
| 'Calypso' | 7.3 (7-8) | 8.0 (7-9) | 8.2 (7-9) | 7.7 (7-8) | 7.7 (6-9) |
| 'Jersey' | 6.0 (all 6s) | 6.0 (all 6s) | 5.5 (5-6) | 7.0 (all 7s) | 7.0 (6-8) |
| 'Legacy' | 7.0 (all 7s) | 7.0 (all 7s) | 7.2 (6-8) | 7.0 (all 7s) | 7.0 (6-8) |
| 'Liberty' | 8.0 (all 8s) | 8.0 (7-9) | 8.0 (all 8s) | 8.5 (8-9) | 8.3 (7-9) |

[1]A sharp temperature reduction in the winter of 2011 damaged a high proportion of the flower buds of most cultivars. 'Calypso' suffered comparable damage to 'Liberty' (about 25%) and had much less damage than 'Legacy' (about 60%).

As illustrated in Table 4, below, the fruit weight of 'Calypso' was the largest of all cultivars across most years and locations. Specifically, average fruit physical and biochemical characteristics of 'Calypso' were compared to standard cultivars in Osorno, Chile (2012) and Grand Junction, Mich. (2011 and 2012). Five-fruit samples were evaluated when the bushes were 30-50% ripe. Levels of soluble solids have been higher than all the standard cultivars except 'Liberty,' and its titratable acidity has generally been higher, except in Chile. This sugar/acid ratio suggests that it is tarter than the other cultivars, although it received higher flavor scores than all of them except 'Liberty.' Therefore, the sugar/acid ratio is perceived as being balanced. The higher acid levels in 'Calypso' may translate into a longer storage life, as high acid fruit are often less subject to fungal rots. The firmness of 'Calypso' was comparable to 'Draper' and 'Liberty' and higher than 'Legacy,' 'Bluecrop,' and 'Jersey.'

TABLE 4

Biochemical Characteristics

| Cultivar | Location | Year | Weight (g) | Soluble solids | Titratable acidity |
|---|---|---|---|---|---|
| Calypso | Michigan | 2011 | 2.4 | 15.2 | 1.26 |
| | | 2012 | 1.8 | 14.3 | 1.30 |
| | Chile | 2012 | 2.8 | 15.9 | 0.68 |
| Draper | Michigan | 2011 | 2.1 | 12.7 | 0.89 |
| | | 2012 | 1.7 | 11.9 | 1.05 |
| Bluecrop | Michigan | 2011 | 1.6 | 11.1 | 0.80 |
| | | 2012 | 1.6 | 11.8 | 0.67 |

TABLE 4-continued

Biochemical Characteristics

| | | | | | |
|---|---|---|---|---|---|
| Legacy | Michigan | 2011 | 2.0 | 12.1 | 0.73 |
| | | 2012 | 2.1 | 13.3 | 0.52 |
| | Chile | 2012 | 2.2 | 13.8 | 0.40 |
| Liberty | Michigan | 2011 | 1.8 | 15.4 | 0.85 |
| | | 2012 | 1.7 | 15.8 | 0.53 |
| | Chile | 2012 | 2.4 | 14.8 | 0.70 |
| Jersey | Michigan | 2011 | 1.4 | 13.2 | 0.51 |
| | | 2012 | 1.2 | 13.8 | 0.63 |

| Cultivar | Location | Year | SS/TA | Firmness (g/mm) | Firmness (N) |
|---|---|---|---|---|---|
| Calypso | Michigan | 2011 | 12.1 | — | — |
| | | 2012 | 11.0 | 330 | — |
| | Chile | 2012 | 23.4 | — | 40.1 |
| Draper | Michigan | 2011 | 14.3 | — | — |
| | | 2012 | 12.1 | 334 | — |
| Bluecrop | Michigan | 2011 | 13.9 | — | — |
| | | 2012 | 17.6 | 202 | — |
| Legacy | Michigan | 2011 | 16.6 | — | — |
| | | 2012 | 25.6 | 301 | — |
| | Chile | 2012 | 34.5 | — | 37.6 |
| Liberty | Michigan | 2011 | 18.2 | — | |
| | | 2012 | 29.8 | 322 | |
| | Chile | 2012 | 21.1 | | 43.1 |
| Jersey | Michigan | 2011 | 25.9 | — | — |
| | | 2012 | 21.9 | 202 | — |

As illustrated in Table 5, the fruit of 'Calypso' is large and more firm relative to the fruit of 'Jersey.' Relative to the fruit of 'Legacy,' the fruit of 'Calypso' has a very small picking scar and is much firmer.

TABLE 5

Expression Characteristics

| Cultivar | Characteristic | Expression of the characteristic in the cultivar | Expression of the characteristic in 'Calypso |
|---|---|---|---|
| 'Jersey' | fruit size | small to medium | large |
| 'Jersey' | fruit firmness | moderately soft | firm |
| 'Legacy' | picking scar | medium to small | very small |
| 'Legacy' | fruit firmness | moderately firm | very firm |

'Calypso' is distinct from its female parent 'Draper' in that 'Calypso' plants have: larger fruit; sweeter fruit; stronger winter hardiness, higher yields (Michigan growth trials), more vigor, higher levels of soluble solids in fruit and a later harvest. 'Calypso' is similar to its seed parent 'Draper' in that 'Calypso' plants have: an overlapping fruiting season; similar fruit firmness, and similar soluble fruit solids.

'Calypso' is distinct from its pollen parent 'Elliot' in that 'Calypso' plants have larger, more firm and lighter colored fruit, higher soluble sugars and an earlier harvest. They are similar in productivity.

What is claimed is:

1. A new and distinct highbush blueberry plant, substantially as illustrated and described herein.

* * * * *